United States Patent [19]

Santi et al.

[11] Patent Number: 4,584,145
[45] Date of Patent: Apr. 22, 1986

[54] PROCESS FOR PREPARING CARBONYL COMPOUNDS

[75] Inventors: Roberto Santi, Novara; Giuseppe Cometti, Verbania-Pallanza; Anselmo Pagani, Trecate, all of Italy

[73] Assignee: Montedison S.p.A., Milan, Italy

[21] Appl. No.: 746,305

[22] Filed: Jun. 19, 1985

[30] Foreign Application Priority Data

Jun. 20, 1984 [IT] Italy ............................ 21520 A/84

[51] Int. Cl.⁴ .................. C07C 121/76; C07C 69/716
[52] U.S. Cl. .................................. 558/406; 558/410; 558/443; 560/145; 560/176
[58] Field of Search ......... 260/465 D, 465.4, 465.8 R; 560/145, 176

[56] References Cited

U.S. PATENT DOCUMENTS 3,560,569  2/1971  Hurd ................................. 560/176

Primary Examiner—Dolph H. Torrence
Attorney, Agent, or Firm—Patricia Q. Peake

[57] ABSTRACT

There is described a process for preparing carbonyl compounds of formula:

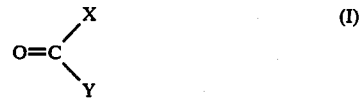

by oxidation of compounds of formula:

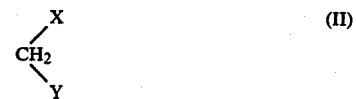

wherein X=—CN, —COOR, Y=—COOR₁, —CN, and R, R₁, like or unlike each other, are inert radicals, by employing oxygen or air as oxidants, at least a catalyst selected from the salts of organic or inorganic acids of Mn, Co, Cu and Fe, from 0 to 60 moles of an alkaline salt of an aliphatic carboxylic acid per gram-atom of catalyst metal, in a polar solvent, at temperatures ranging from 30° C. to 200° C. and maintaining the reaction medium anhydrous.

The present invention relates to a process for preparing carbonyl compounds by catalytic oxidation of compounds containing an activated methylene group.

11 Claims, No Drawings

PROCESS FOR PREPARING CARBONYL COMPOUNDS

BACKGROUND OF THE INVENTION

Methods are known for preparing carbonyl compounds by direct oxidation of compounds containing an activated methylene group, such as for example the esters of malonic acid, by using, as oxidants, tri- and tetravalent oxides of nitrogen, bromine or selenium dioxide.

Such methods, however, besides requiring the use of toxic and dangerous oxidants, are not catalytic and provide only low yields, wherefore they are expensive and furthermore little reproducible and generalizable, so that they are difficult to be industrially produced, particularly for large-scale productions.

DESCRIPTION OF THE INVENTION

The object of the present invention is to obtain by direct oxidation of compounds containing an activated methylene group, high yields of corresponding carbonyl compounds, without using toxic or dangerous oxidants, by employing a simple, economic and easily generalizable method.

It has now been found that the aforesaid objects are attained by using, as an oxidant, oxygen or air in the presence of particular metallic catalysts.

Thus, it is the object of the present invention to provide a process for preparing carbonnyl compounds of formula:

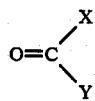

(I)

by direct oxidation of compounds containing an activated methylene group of formula:

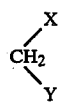

(II)

in which X is an organic radical selected from —CN, —COOR and Y is an organic radical selected from —COOR₁ and —CN, wherein R and R₁, like or unlike each other, are inert organic substituents under the reaction conditions, characterized in that the oxidation of the compound of formula II is carried out by employing oxygen or air as oxidants, in the presence of at least a catalyst selected from the salts of Mn, Co, Cu and Fe of organic or inorganic acids, and of 0–60 moles of an alkaline salt of an aliphatic carboxylic acid per gram-atom of catalyst metal, in a reaction medium consisting of a polar solvent in which the catalyst can be soluble, at a temperature ranging from 30° C. to 200° C. and maintaining the reaction medium anhydrous.

Substituents R and R₁ of radicals X and Y of the compounds of formula (I) and (II) may be, for example, alkyls containing from 1 to 6 carbon atoms, cycloalkyls, aryls, substituted aryls.

The reaction can be conducted either at atmospheric pressure, with an oxygen or air flow of at least 2 l/hour, or at pressures ranging from 1 to 50 atmospheres of the abovesaid gases.

The catalyst is preferably selected from the salts of Mn, Co, Cu and Fe of carboxylic acids and, among these, the acetates are the best preferred.

It is particularly advantageous to utilize a cobalt salt combined with a manganese salt in a molar ratio of 1:1, expressed as metal.

The catalyst is employed in catalytic amounts, generally ranging from 0.03 to 0.003 gram-atoms of metal contained in the catalyst per mole of compound of formula (II).

The alkaline salt of an aliphatic carboxylic acid is preferably selected from the sodium or potassium acetates, and it is employed in amounts not exceeding 60 moles, preferably in amounts from 10 to 20 moles, per gram-atom of metal contained in the catalyst.

The polar solvent in which the catalyst is soluble is preferably selected from the aliphatic carboxylic acids containing up to 5 atoms of carbon, in particular acetic acid.

The reaction medium is maintained anhydrous by adding an anhydride, preferably acetic anhydride, or by removing the water which forms during the reaction by continuous azeotropic distillation with a proper solvent, preferably selected from the aromatic hydrocarbons.

The reaction temperature is suitably selected in the range from 30° to 200° C. as a function of the composition of the reaction mixture and of the reaction rate to be obtained.

At the end of the reaction, the resulting carbonyl compound is separated from the reaction mixture by means of substantially conventional techniques, such as e.g. distillation.

It is also possible to recover the catalyst from the reaction mixture, in order to recycle it to the system.

The process according to the present invention, other than the processes of the prior art, permits to obtain the carbonyl compounds of formula (I) with high yields, avoiding the use of toxic or dangerous oxidants, with a good control of the reaction and, by consequence, with a simple and economic procedure, which is suited to be adopted for commercial-scale productions.

The carbonyl compounds of formula (I) are important intermediates for the synthesis of organic products in the fine chemistry field, in particular in the pharmaceutical field and in the one of the additives for plastics.

In fact they possess a highly reactive carbonyl functionality which is capable of providing very interesting addition products for the synthesis of fine chemicals.

Thus, for example, the esters of mesoxalic acid, which are obtained by the present process, when reacted with alkyl or aryl halides in the presence of the Zn/Cu metal pair, give rise to the series of the alkyl- or aryl-tartronic acids, which are of great interest for pharmaceutical preparations.

The following examples are given to illustrate the invention, without being however a limitation thereof.

EXAMPLE 1

0.25 g (1.1 m.moles) of (CH₃COO)₃Co, 0.25 g (1.1 m.moles) of (CH₃COO)₃Mn, 1.5 g (18.3 m.moles) of sodium acetate, 10 g (62,4 m.moles) of ethyl malonate dissolved in 15 ml of acetic acid and 6.5 ml of acetic anhydride were introduced into a reactor equipped with stirrer, reflux cooler, temperature-adjusting and oxygen-feed system. 5 l/hour of oxygen were bubbled into the mixture, while maintaining the reaction mixture at a temperature of 130° C. by means of an external oil bath.

After 5 hours, at the end of the reaction, the solvents were removed under vacuum and the residue was distilled under reduced pressure.

Two fractions separated, one of which consisting of 1.5 g of ethyl malonate and the other one consisting of 7.5 g of ethyl mesoxalate, the residue being of 1 g.

A conversion of 85%, a selectively of 81% and therefore a yield of 69% of ethyl mesoxalate were obtained.

EXAMPLE 2

Into a glass 100 ml autoclave equipped with magnetic stirrer there were introduced 0.25 g (1.1 m.moles) of $(CH_3COO)_3Co$, 0.25 g (1.1 m.moles) of $(CH_3COO)_3Mn$, 1.5 g (18.3 m.moles) of sodium acetate, 10 g (62.5 m.moles) of ethyl malonate dissolved in 15 ml of acetic acid and 6.5 ml of acetic anhydride.

3 atm. of oxygen were then charged and the whole was heated to 130° C., maintaining the reaction mixture at such temperature during 7 hours.

At the end, the solvents were removed under vacuum and the residue was distilled under reduced pressure.

5 g of diethyl ketomalonate were separated by distillation.

We claim:

1. A process for preparing a compound of formula:

  (I)

by direct oxidation of a compound of formula:

  (II)

in which X is an organic radical selected from —CN, —COOR and Y is an organic radical selected from —COOR$_1$ and —CN, wherein R and R$_1$, like or unlike each other, are inert organic substituents in the reaction conditions, characterized in that the oxidation of the compound of formula (II) is accomplished by using oxygen or air as oxidants, in the presence of at least a catalyst selected from the salts of Mn, Co, Cu and Fe of organic or inorganic acids, and of 0–60 moles of an alkaline salt of an aliphatic carboxylic acid per gram-atom of catalyst metal, in a reaction medium consisting of a polar solvent in which the catalyst may be soluble, at a temperature ranging from 30° to 200° C. and maintaining the reaction medium anhydrous.

2. The process according to claim 1, in which substituents R and R$_1$ are selected from the group consisting of the alkyls containing from 1 to 6 carbon atoms, the cycloalkyls, aryls and substituted aryls.

3. The process according to claim 1, in which the catalyst is selected from the group consisting of the salts of Mn, Co, Cu and Fe of carboxylic acids.

4. The process according to claim 1, in which the catalyst is selected from the group consisting of the acetates of Mn, Co, Cu and Fe.

5. The process according to claim 1, in which, as a catalyst, a cobalt salt combined with a manganese salt in a molar ratio of 1/1, expressed as metal, is employed.

6. The process according to claim 1, in which the catalyst is employed in amounts ranging from 0.03 to 0.003 gram-atoms of metal contained in the catalyst per mole of compound of formula (II).

7. The process according to claim 1, in which from 10 to 20 moles of alkaline salt per gram-atom of catalyst metal are employed.

8. The process according to claim 1, in which the alkaline salt is selected from the group consisting of sodium and potassium acetate.

9. The process according to claim 1, in which the polar solvent is selected from the group consisting of aliphatic carboxylic acids containing up to 5 carbon atoms.

10. The process according to claim 1, in which acetic acid is employed as a solvent.

11. The process according to claim 1, which the reaction medium is maintained anhydrous by addition of acetic anhydride.

* * * * *